(12) United States Patent
Cohen

(10) Patent No.: US 9,149,640 B2
(45) Date of Patent: Oct. 6, 2015

(54) PACING SYSTEMS FOR TREATING FUNCTIONAL VENTRICULAR CONDUCTION ABNORMALITIES OF INTRINSIC ORIGIN INCORPORATING IMPROVED ELECTROCARDIOGRAPHIC ACQUISITION APPARATUS AND METHODS

(76) Inventor: Fred Michael Cohen, Phoenix, AZ (US)

( * ) Notice: Subject to any disclaimer, the term of this patent is extended or adjusted under 35 U.S.C. 154(b) by 187 days.

(21) Appl. No.: 13/544,926

(22) Filed: Jul. 9, 2012

(65) Prior Publication Data
US 2014/0012343 A1 Jan. 9, 2014

(51) Int. Cl.
A61N 1/365 (2006.01)
A61N 1/05 (2006.01)
A61B 5/0452 (2006.01)

(52) U.S. Cl.
CPC .......... *A61N 1/36592* (2013.01); *A61B 5/0452* (2013.01); *A61N 1/056* (2013.01); *A61N 1/365* (2013.01)

(58) Field of Classification Search
CPC .............................. A61B 5/0452; A61N 1/365
USPC ....................................................... 607/17, 25
See application file for complete search history.

(56) References Cited

U.S. PATENT DOCUMENTS

| | | | |
|---|---|---|---|
| 5,702,425 A * | 12/1997 | Wickham | 607/25 |
| 6,267,778 B1 * | 7/2001 | Cohen | 607/9 |
| 2002/0087055 A1 * | 7/2002 | Rowlandson | 600/301 |
| 2002/0151806 A1 * | 10/2002 | Starobin et al. | 600/509 |
| 2004/0044374 A1 * | 3/2004 | Weinberg et al. | 607/25 |

* cited by examiner

*Primary Examiner* — Joseph Dietrich
(74) *Attorney, Agent, or Firm* — Robert A. Parsons; Michael W. Goltry; Parsons & Goltry

(57) ABSTRACT

Therapeutic implantable cardiac pacing systems incorporating improved electrocardiographic acquisition systems for the purpose of ventricular pacing during wide QRS complexes of intrinsic origin, in order to narrow the QRS complex in patients where QRS narrowing is achievable and improving ventricular function in all patients with wide QRS complexes including those where QRS shortening does not result. These pacing systems are employed to increase coronary artery flow and electrode position is employed to improve ventricular motion in the treatment of functional ventricular abnormalities caused by wide QRS complexes.

16 Claims, 5 Drawing Sheets

Onset of QRS and ventricular activation as determined from earliest detection of QRS onset - in this example lead V1

Delay of detected QRS onset due to cancellation of positive and negative electrical vectors producing an initial isoelectric interval - in this example lead II

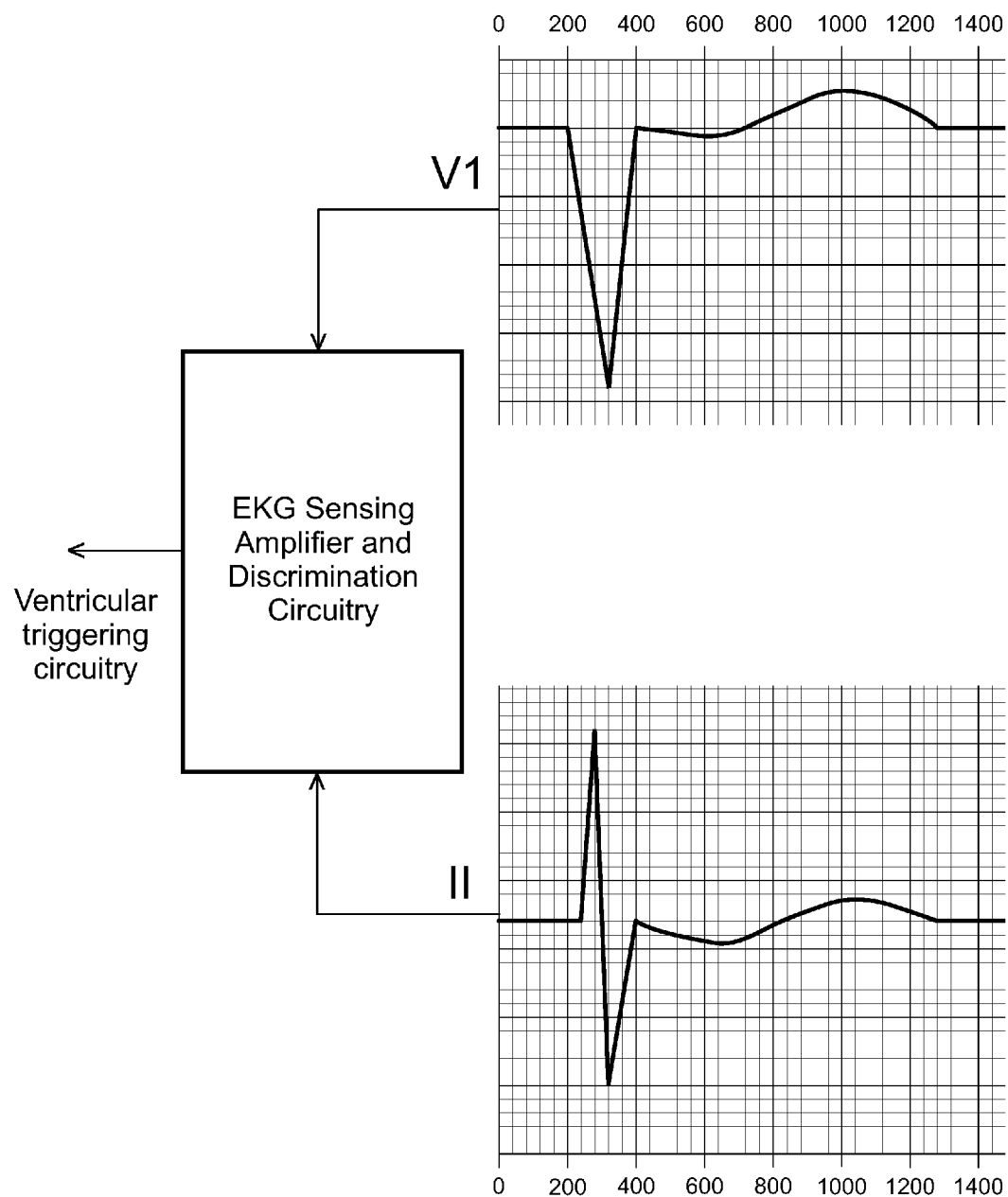

PACING SYSTEMS FOR TREATING FUNCTIONAL VENTRICULAR CONDUCTION ABNORMALITIES OF INTRINSIC ORIGIN INCORPORATING IMPROVED ELECTROCARDIOGRAPHIC ACQUISITION APPARATUS AND METHODS

REFERENCES CITED

U.S. PATENT DOCUMENTS

| | | |
|---|---|---|
| 3,893,461 | July 1975 | Preston. |
| 4,088,149 | May 1978 | Rockland et al. |
| 4,126,139 | November 1978 | Walters et al. |
| 4,444,195 | April 1984 | Gold. |
| 4,554,922 | November 1985 | Prystokowsky et al. |
| 4,628,934 | December 1986 | Pondorf et al. |
| 4,787,389 | November 1988 | Tarjan. |
| 4,928,688 | May 1990 | Mower. |
| 4,967,749 | November 1990 | Cohen. |
| 5,018,523 | May 1991 | Bach Jr. et al. |
| 5,312,445 | May 1994 | Nappholz et al. . . . 607/9 |
| 5,609,158 | March 1997 | Chan. |

FOREIGN PATENT DOCUMENTS

| | | |
|---|---|---|
| 0030897 | June 1981 | (EP). |

Other Publications

Danzig M D, Robertson T L, Webber L S, Day G, Dock D S: Earliest Onset of QRS in Anterior Precordial ECG Leads: Precision of Time Interval Measurements. Circulation 54: 447-451, 1976

Wong G K, Florendo F T, Cohen F M: Ventricular Activation Onset-Triggered Left Ventricular Pacing: Safety and Feasibility in Initial Clinical Experience. PACE 27: 730-739, 2004

BACKGROUND OF THE INVENTION

This invention relates generally to medicine and more specifically to improved cardiac pacing systems including methods of pacing and sensing in the treatment of cardiac disease. Reference is hereby made to my U.S. Pat. Nos. 5,174,289, 5,267,560 and 6,267,778 which are incorporated herein by reference. These patents define terms that will be used herein, describe limitations of previous pacing systems and contain prior art and classification information that may be applicable to this invention. In particular, U.S. Pat. No. 6,267,778 describes pacing apparatus and methods that employ the acquisition of an EKG to trigger ventricular pacing. This invention will describe improved apparatus and methods for the acquisition of an EKG to trigger ventricular pacing.

BRIEF SUMMARY OF THE INVENTION

One object of the present invention is to provide apparatus and methods for improved acquisition of EKG signals incorporating the analysis of multiple EKG signals for the purpose of avoiding the delay in determining the QRS onset when an EKG lead may exhibit an initial isoelectric QRS complex.

Another object of the present invention is to provide apparatus and methods for improved acquisition of EKG signals of varying morphologies as for example may result from complete left bundle branch block and premature ventricular contractions when the variation in morphology may produce a variation in which lead the particular QRS complex may exhibit an initial isoelectric interval.

An additional object of the present invention is to provide mode switching when electrical interference is detected in a single EKG lead amplifier.

A further objective of the present invention is provide multiple EKG lead amplifiers where an electrical interference signal on one amplifier, detected as a high rate, causes the elimination of the amplifier from signal detection. In the case of multiple amplifiers mode switching occurs when at least two amplifiers detect electrical interference.

According to the present invention at least two EKG leads are monitored to determine the earliest onset of the QRS signal in an individual QRS complex. When various QRS complexes are considered the monitoring of multiple leads results in the selection of the signal which produces the earliest QRS onset when the lead from which a particular QRS complex onset is detected may vary from the lead at which another QRS complex onset is detected. At least one EKG lead may be connected to a sensing amplifier and at least two sensing amplifiers may be employed to discriminate between at least two EKG leads to determine and document the delay in a particular amplifier with respect to another amplifier and to detect electrical interference on one amplifier which may not exist in another amplifier. The use of at least two sensing amplifiers provides apparatus for and methods of mode switching only when electrical interference is detected on at least two leads.

The foregoing and other objects, features and advantages of the invention will be apparent from the following, more particular description of the preferred embodiment of the invention, as illustrated in the accompanying drawings.

BRIEF DESCRIPTION OF THE SEVERAL VIEWS OF THE DRAWING

FIG. 3 illustrates the schematic representation of two different EKG leads in the same patient connected in parallel to an EKG sensing amplifier so that the first detected QRS onset is sensed by the device regardless of which lead it occurs in.

DETAILED DESCRIPTION OF THE INVENTION

This invention will describe novel methods and apparatus for improved acquisition of an EKG signal in patients who exhibit wide QRS complexes of intrinsic origin and are treated for their resulting ventricular dysfunction by ventricular pacing triggered by intrinsic QRS onset detection. Whereas, in the medical literature certain surface EKG signals are referred to as standard lead configurations, it should be noted that EKG signals obtained from implanted electrodes may not conform to standard lead configurations. Thus the terms "lead," "signal" and "configuration" will be used synonymously in this description of the preferred embodiment of this invention, when referring to an EKG. The term "lead" will be used herein to conform to the medical literature standard configuration with the understanding that when applied in an implantable configuration the signal may not exactly match the standard configuration. Whereas different standard leads produce different signals, different implantable configurations which are not standard also produce different signals.

Figure 1A:
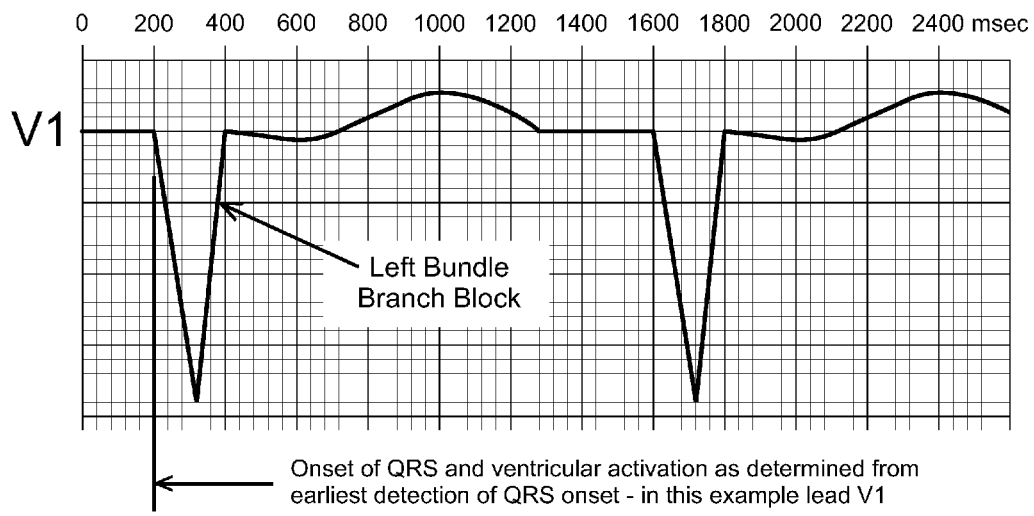
FIG. 1a illustrates a lead V1 electrocardiogram in a patient with left bundle branch block. P waves are not shown on this EKG as this hypothetical patient is in sinus arrest with an atrioventricular nodal rhythm.
Figure 1B:
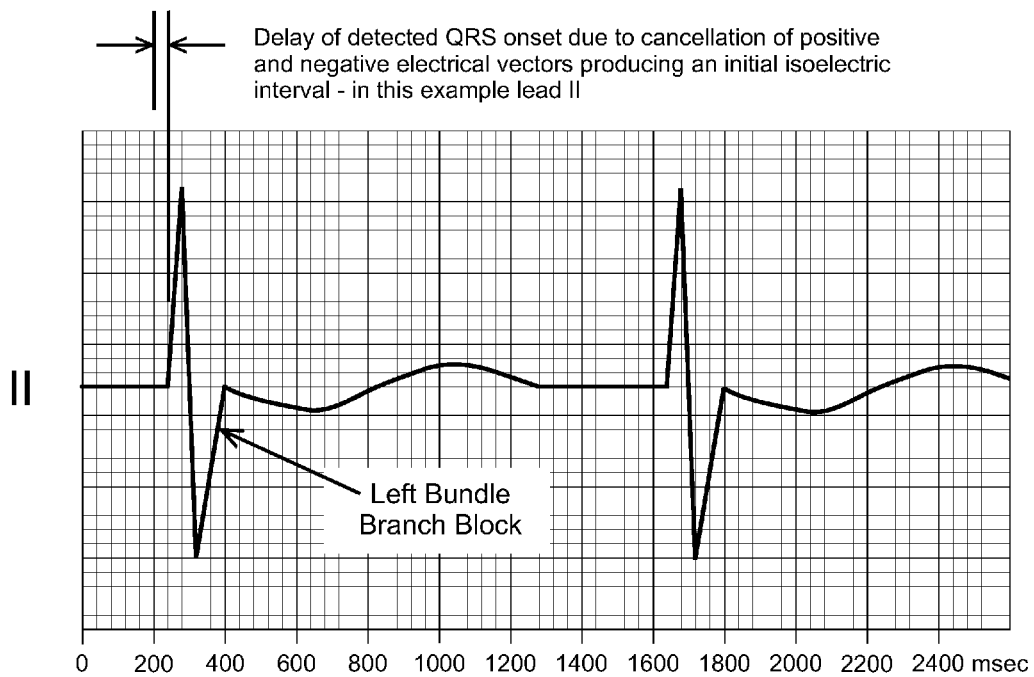
FIG. 1b illustrates a lead II electrocardiogram in the same patient with left bundle branch block as FIG. 1a recorded simultaneously with the lead V1 electrocardiogram. When comparing FIG. 1a to FIG. 1b, the detected onset of the QRS in lead V1 precedes the detected onset of the QRS in lead II.
Figure 2A:
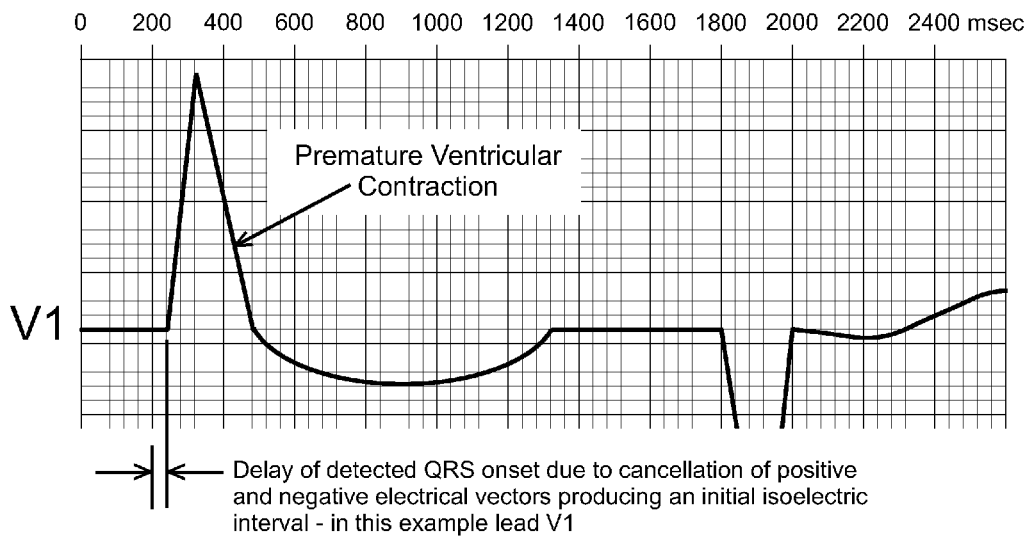
FIG. 2a illustrates a lead V1 electrocardiogram in the same patient as FIGS. 1a and 1b, while a premature ventricular contraction occurs prior to the left bundle branch tracing.
Figure 2B:
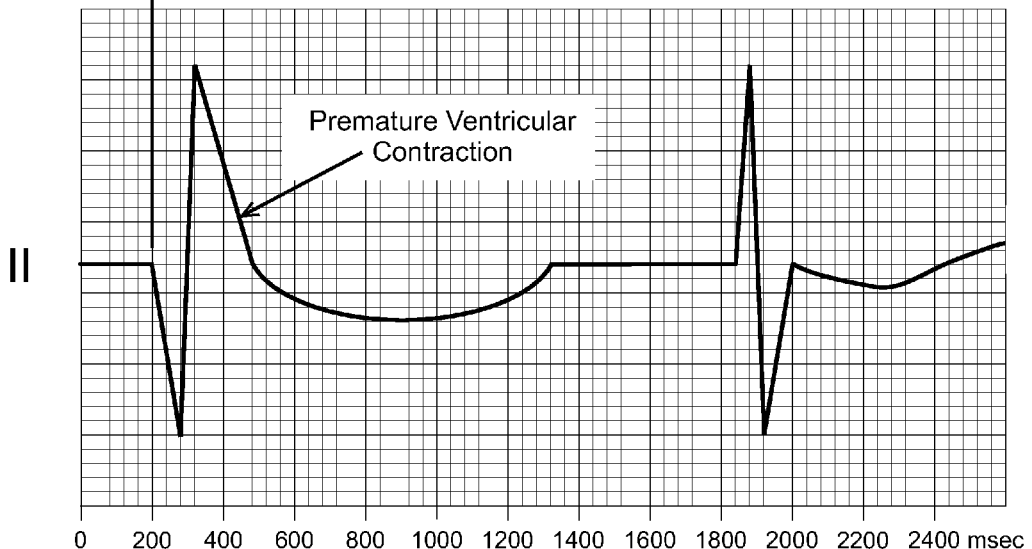
FIG. 2b illustrates a lead II electrocardiogram in the same patient as FIGS. 1a, 1b and 2a, recorded simultaneously with the electrocardiogram in FIG. 2a while a premature ventricular contraction occurs prior to the left bundle branch tracing. When comparing the premature ventricular contractions in FIG. 2a to FIG. 2b, the detected onset of the QRS in lead II precedes the detected onset of the QRS in lead VI.

The origins of a QRS complex also known as the electrical signal denoting ventricular electrical activation consist of electrical vectors produced by the depolarization of individual cardiac cells within the ventricular muscle as they activate. It is well known in the medical literature that when recording a standard twelve lead surface EKG, the detection of the onset of the QRS complex may be delayed in certain leads due to the presence of initial opposing electrical vectors that result in an initial portion of the QRS becoming isoelectric. This fact may be evident when comparing the QRS onsets of various leads as illustrated in FIGS. 1a & 1b. When various QRS complexes, for example, complete left bundle branch block (LBBB) and a premature ventricular contraction (PVC), are analyzed in an individual patient, at least one lead in which the initial QRS of a LBBB complex is isoelectric may differ from at least one lead in which the initial QRS of a PVC is isoelectric, as illustrated in FIGS. 2a and 2b. Multifocal PVCs may similarly produce variations in at least one lead that exhibits an isoelectric delay in the QRS complex.

When employing a pacing system to stimulate the ventricular muscle triggered by the onset of the QRS complex, it is important for the pacing impulse to occur as early as possible in order for effective coordination of the pacing impulse with intrinsic ventricular function. Thus it is desirable to avoid any delay that is caused by employing a lead that exhibits an initial isoelectric QRS segment. The pacing methods and systems described in U.S. Pat. No. 6,267,778 employ a single sensing amplifier for the detection of the QRS onset from a single EKG configuration. Modification of these systems to detect at least two EKG leads through one sensing amplifier would avoid any delay produced by an initial isoelectric QRS segment in one lead provided another lead more accurately represented the QRS onset as illustrated in FIG. 3. In this configuration the first detected QRS onset in a lead would be employed to trigger ventricular pacing while subsequent QRS onsets in other leads would be undetected as they would occur during the sensing amplifiers refractory period.

Figure 4:
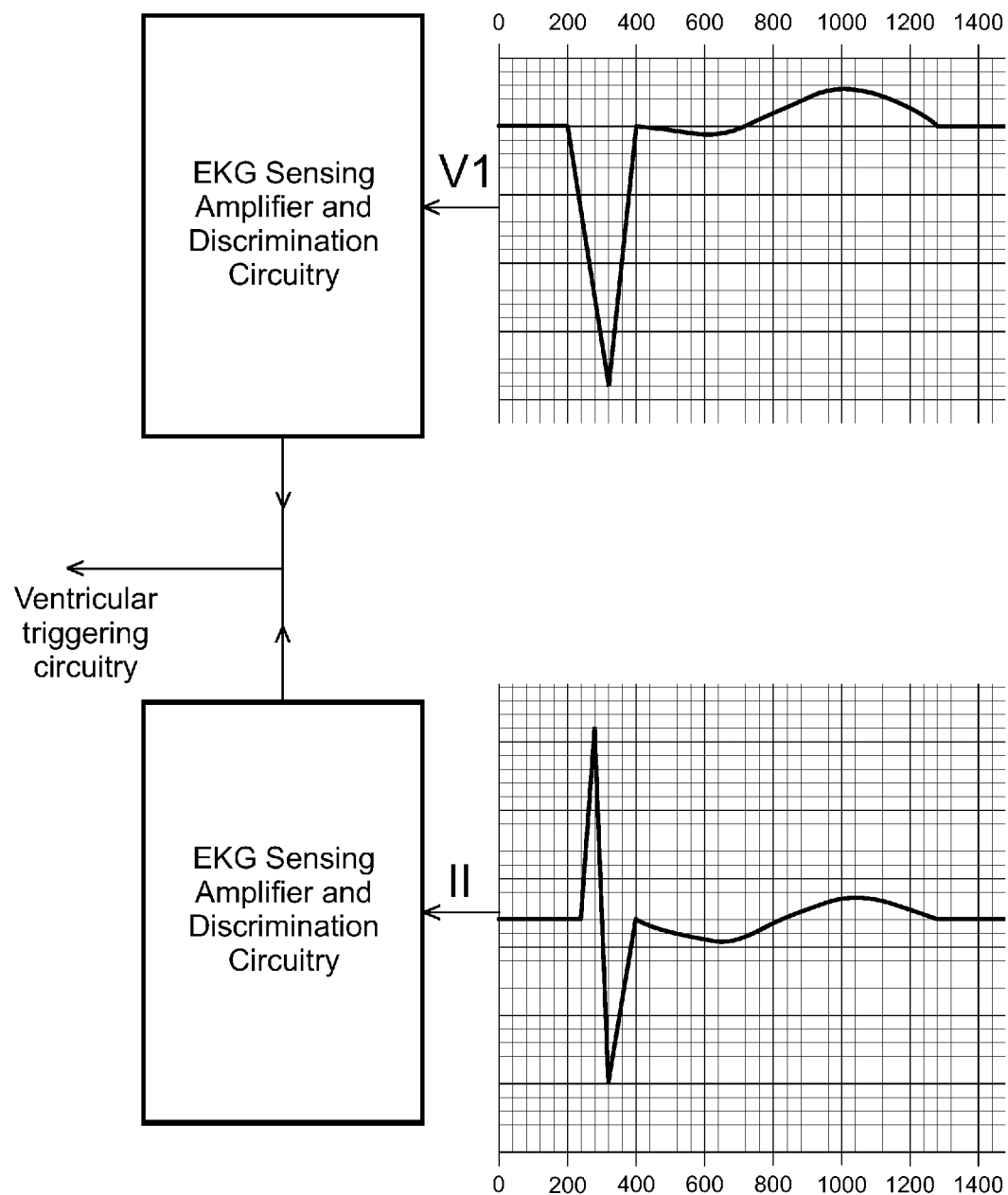
FIG. 4 illustrates the schematic representation of connecting two different EKG sensing amplifiers in parallel with ventricular triggering circuitry, with each amplifier sensing a different EKG lead in the same patient. In this configuration the first detected QRS onset will trigger ventricular pacing and detection of the second QRS onset can provide a means to measure the time between each detected QRS onset.

The determination of which lead is best to employ for QRS onset detection in a particular patient for each particular QRS complex that patient may exhibit would be best performed by employing at least two sensing amplifiers in parallel with at least one EKG lead connected to each sensing amplifier as illustrated in FIG. 4. In this configuration the interval between each QRS onset measured in different amplifiers could be determined and in the case where multiple leads are available, the leads best representing the QRS onset for a particular QRS complex could be employed. Employing at least two amplifiers also would produce the capability of identifying a certain wide QRS complex such as a premature ventricular contraction that characteristically may be sensed initially from at least one lead connected to one amplifier while a normal narrow QRS complex would be sensed initially from at least one other lead connected to another amplifier thus providing a capability to distinguish between wide and narrow QRS complexes. As noted in the prior art it would be advantageous for the pacing system to be programmed to pace into a wide QRS complex while not pacing into a narrow QRS complex to avoid widening the narrow QRS complex.

Figure 5:
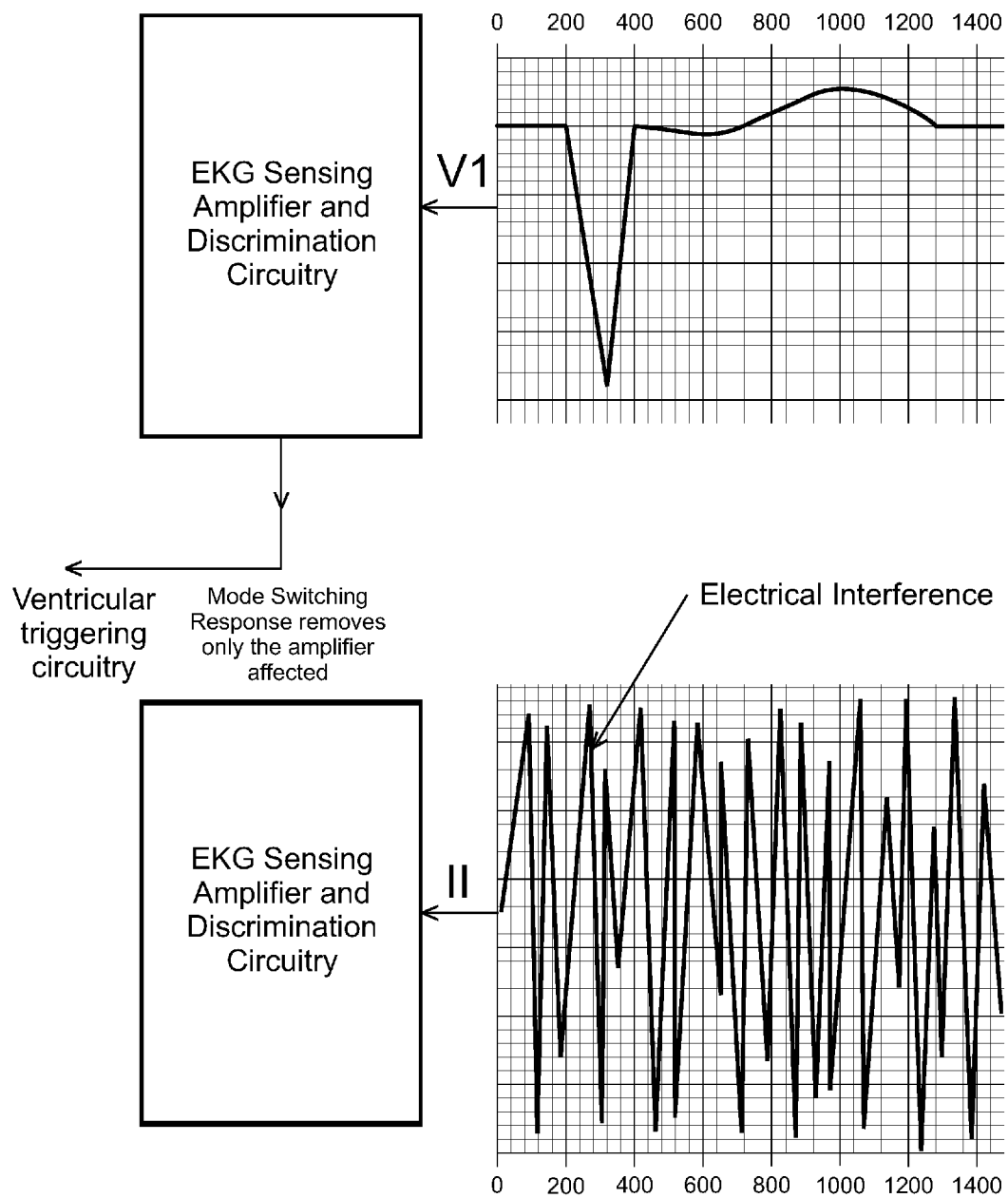
FIG. 5 illustrates the detection of electrical interference on one amplifier, in the configuration of FIG. 4, that is detected by a mode switching circuit modified to turn off the amplifier in the presence of electrical interference on its EKG lead.

Stability of the electrical signal from a particular EKG lead is an important prerequisite for accurately determining the onset of the QRS complex. Electrical interference may occur as a result of peripheral muscle signals, exposure to large electrical fields and other factors. Well known mode switching systems that are employed on the atrial channel of dual chamber pacing systems for the purpose of switching to a ventricular mode when high atrial rates are detected on the atrial sensing channel may be modified to detect electrical interference as a high rate when connected to and sensing an EKG lead, and mode switching, for example, to a biventricular pacing mode. When employing at least two EKG lead sensing amplifiers with at least one EKG lead connected to each amplifier, it would be possible to detect electrical interference at one amplifier while detecting a stable EKG signal at another thus using the detection of electrical interference to ignore the unstable signal of one EKG lead while accurately sensing another unaffected EKG lead as illustrated in FIG. 5. In the case of employing multiple amplifiers mode switching to a biventricular pacing mode could be delayed until at least two amplifiers indicate electrical interference.

I claim:

1. Cardiac electrical stimulation apparatus comprising; first means for acquiring at least two electrocardiographic leads from a patient each detecting an onset of a QRS complex; second means responsive to said first means for determining a first of the detected onsets of the QRS complex from the at least two electrocardiographic leads; and third means having output means and responsive to said second means for providing at least one stimulating impulse to at least one ventricular location simultaneous with said first detected onset of the QRS complex within a predetermined time interval and providing at least one stimulating impulse to at least one said ventricular location in the absence of the detection of any onset of any QRS complex within said predetermined interval.

2. Apparatus according to claim 1 additionally comprising fourth means, to which said third means is responsive, for providing inhibition of at least one said stimulating impulse to at least one said ventricular location upon the detection of intrinsic ventricular activity at, at least one ventricular location within said predetermined time interval.

3. Apparatus according to claim 2 wherein the second means includes the capability to switch pacing modes on the detection of electrical interference.

4. Apparatus according to claim 2 wherein the second means comprises at least two sensing amplifiers with at least one electrocardiographic lead connected to each sensing amplifier.

5. Apparatus according to claim 4 wherein the second means includes the capability to switch an amplifier off upon the detection of electrical interference at that amplifier.

6. Apparatus according to claim 5 wherein switching pacing modes requires at least two amplifiers to detect electrical interference.

7. A method for improving the ventricular function of the heart of a patient comprising the steps of:
   (a) acquiring at least two electrocardiographic leads (EKGs) from a patient, each detecting an onset of a QRS complex;
   (b) electronically analyzing said EKGs to determine the first detected onset of the QRS complex of intrinsic origin;
   (c) placing at least one electrode to stimulate the ventricular muscle at, at least one location selected to improve the ventricular function of the patient's heart upon ventricular stimulation simultaneous with said first detected onset of the QRS complex;
   (d) electrically connecting at least one of said electrodes to a pacing system;
   (e) employing said first detected onset of the QRS complex within a predetermined time interval to stimulate the ventricular muscle at, at least one said ventricular location, simultaneous with said first detected onset of the QRS complex and employing the absence of an onset of the QRS complex within said predetermined time interval to stimulate the ventricular muscle at, at least one said ventricular location.

8. The method of claim 7 wherein ventricular electrical activity at, at least one said ventricular electrode within said predetermined time interval inhibits the deliverance of said ventricular stimulation to at least one said ventricular electrode.

9. The method of claim 7 wherein the step of electronically analyzing said EKGs (b) includes a method of mode switching in the presence of electrical interference.

10. The method of claim 8 wherein the step of electronically analyzing said EKGs (b) employs at least two sensing amplifiers with at least one EKG lead connected to each amplifier.

11. The method of claim 10 wherein the detection of electrical interference at an amplifier turns off the amplifier.

12. The method of claim 11 wherein the detection of electrical interference at, at least two amplifiers switches pacing modes.

13. Cardiac electrical stimulation apparatus comprising:
   means for stimulating the ventricular muscle triggered by the detection of a QRS onset from an EKG configuration in the presence of a detected QRS onset during a predetermined time interval and stimulating the ventricular muscle in the absence of a said detected QRS onset during said predetermined time interval;
   Second means for sensing at least two EKG configurations to determine the first QRS onset detected and employing said first QRS onset to trigger ventricular stimulation.

14. Apparatus according to claim 13 additionally comprising at least two EKG sensing amplifiers with at least one EKG lead connected to each to determine the time interval between each amplifier's earliest detected QRS onset.

15. Apparatus according to claim 14 additionally comprising apparatus for distinguishing between wide and narrow EKG complexes of intrinsic origin based on identifying the EKG configuration that is isoelectric for a particular EKG complex at a particular EKG amplifier.

16. Apparatus according to claim 15 additionally comprising apparatus for triggering ventricular pacing when a wide QRS complex is detected and inhibiting ventricular pacing when a narrow QRS complex is detected, within the predetermined time interval.

* * * * *